(12) United States Patent
Hofen et al.

(10) Patent No.: US 6,610,865 B2
(45) Date of Patent: Aug. 26, 2003

(54) PROCESS FOR THE EPOXIDATION OF OLEFINS

(75) Inventors: Willi Hofen, Rodenbach (DE); Georg Thiele, Hanau (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/222,343

(22) Filed: Aug. 15, 2001

(65) Prior Publication Data

US 2003/0040636 A1 Feb. 27, 2003

Related U.S. Application Data

(60) Provisional application No. 60/312,065, filed on Aug. 15, 2001.

(51) Int. Cl.$^7$ ............................................. C07D 301/12
(52) U.S. Cl. ........................................ 549/531; 549/523
(58) Field of Search ................................. 549/531, 523

(56) References Cited

U.S. PATENT DOCUMENTS

| | | | |
|---|---|---|---|
| 2,870,171 A | 1/1959 | Gable | |
| 4,410,501 A | 10/1983 | Taramasso et al. | |
| 4,833,260 A | 5/1989 | Neri et al. | |
| 5,523,426 A | 6/1996 | Jubin, Jr. et al. | |
| 5,591,875 A | 1/1997 | Chang et al. | |
| 5,599,955 A | 2/1997 | Vora et al. | |
| 5,620,935 A | 4/1997 | Thiele | |
| 5,675,026 A | 10/1997 | Thiele | |
| 5,760,253 A | 6/1998 | Danner et al. | |
| 5,849,937 A | 12/1998 | Jubin, Jr. et al. | |
| 5,849,938 A | 12/1998 | Rueter et al. | |
| 5,912,367 A | 6/1999 | Chang | |
| 6,042,807 A | 3/2000 | Faraj | |
| 6,063,941 A | 5/2000 | Gilbeau | |
| 6,372,924 B2 | 4/2002 | Thiele | |

FOREIGN PATENT DOCUMENTS

| | | |
|---|---|---|
| DE | 198 35 907 | 2/2000 |
| DE | 19723950 | 10/2001 |
| EP | 0 100 118 | 2/1984 |
| EP | 0 100 119 | 2/1984 |
| EP | 0 106 671 | 4/1984 |
| EP | 0 230 349 | 7/1987 |
| EP | 0 230 949 | 8/1987 |
| EP | 0 568 336 | 11/1993 |
| EP | 0 568 337 A2 | 11/1993 |
| EP | 0 583 828 | 2/1994 |
| EP | 0 645 473 | 3/1995 |
| EP | 0 659 473 A1 | 6/1995 |
| EP | 0 712 852 | 5/1996 |
| EP | 0 719 768 | 7/1996 |
| EP | 0 757 045 | 2/1997 |
| EP | 0 795 537 | 9/1997 |
| EP | 0 827 765 | 3/1998 |
| EP | 0 930 308 | 7/1999 |
| EP | 0 936 219 | 8/1999 |
| EP | 1 122 248 | 8/1999 |
| EP | 1 066 711 | 12/1999 |
| EP | 1 221 442 | 7/2002 |
| JP | 2166636 | 6/1990 |
| WO | WO 97/47613 | 12/1997 |
| WO | WO 97/47614 | 12/1997 |
| WO | WO 99/01445 | 1/1999 |
| WO | WO 99/07690 | 2/1999 |
| WO | WO 99/11639 | 3/1999 |
| WO | WO 00/07695 | 2/2000 |
| WO | WO 00/17178 | 3/2000 |

OTHER PUBLICATIONS

European Search Report for European Patent Application No. 01 11 9565, dated Jan. 17, 2002, 6 pps.

*Primary Examiner*—Ba K. Trinh
(74) *Attorney, Agent, or Firm*—Smith, Gambrell & Rusell, LLP

(57) ABSTRACT

A process for the catalytic epoxidation of olefins with hydrogen peroxide in a continuous flow reaction system, wherein the reaction mixture includes at least one liquid phase which is passed through a fixed catalyst bed positioned between parallel heat exchange plates and the reaction heat is at least partially removed during the course of the reaction by passing a cooling medium through the heat exchange plates.

30 Claims, No Drawings

PROCESS FOR THE EPOXIDATION OF OLEFINS

REFERENCE TO A RELATED APPLICATION

Provisional patent application 60/312,065 filed Aug. 15, 2001 is relied on and incorporated herein by reference.

INTRODUCTION AND BACKGROUND

The present application relates to a process for the catalytic epoxidation of olefins with hydrogen peroxide in a continuous flow reaction system.

From EP-A 100 119 it is known that olefins can be converted by hydrogen peroxide into olefin oxides if a titanium-containing zeolite is used as catalyst.

Unreacted hydrogen peroxide cannot be recovered economically from the epoxidation reaction mixture. Furthermore, unreacted hydrogen peroxide involves additional effort and expenditure in the working up of the reaction mixture. The epoxidation of propene is therefore preferably carried out with an excess of propene and up to a high hydrogen peroxide conversion. In order to achieve a high hydrogen peroxide conversion it is advantageous to use a continuous flow reaction system. Such a reaction system may comprise either one or more flow reactors or an arrangement of two or more mixing reactors connected in series. Examples of mixing reactors are stirred tank reactors, recycle reactors, fluidized bed reactors and fixed bed reactors with recycling of the liquid phase.

In order to achieve a high reaction rate a high propene concentration in the liquid phase is necessary. The reaction is therefore preferably carried out under a propene atmosphere at elevated pressure with the effect that a multiphase reaction system is in general present.

Furthermore, the epoxidation of olefins with hydrogen peroxide is like most oxidation reactions highly exothermic. Thus, precautions have to be taken to ensure sufficient removal of the heat generated by the exothermic reaction in order to control the reaction. This problem is especially pronounced in continuous flow systems using fixed bed reactors. Moreover conversion and product selectivity in epoxidation reactions of olefins are highly susceptible to temperature changes with the effect that efficient temperature control is of uppermost importance.

In WO 97/47614 with reference to example 8 reaction of propene with hydrogen peroxide using a fixed bed tubular reactor having a cooling jacket in up-flow operation is described. But yield and product selectivity are still insufficient for commercial purposes.

Especially in highly exothermic reactions like epoxidation reactions, effective removal of the heat of reaction is very important. When using fixed bed tubular reactors with cooling jacket like in WO 97/47614 it might become difficult to control heat generation within the catalyst packing inside the reactor. One possibility to overcome this problem is to use tube bundle reactors wherein the catalyst is either (a) packed within the single tubes or (b) outside the single tubes. To ensure the uniform heat dissipation that is essential to exothermic reactions in the first case (a) tube diameter has to be small and in latter case (b) the distance between single tubes has to be small. Both possibilities create problems when designing the reactor. Operation of those tube bundle reactors having a high number of single tubes is likewise difficult since these reactors are susceptible to blocking and fouling. Furthermore, filling with catalyst to ensure uniform packing of the catalyst bed and exchange of deactivated catalyst for regeneration is becoming increasingly difficult with increased number of tubes or reduced distance between single tubes.

EP-A 659 473 describes an epoxidation process wherein a liquid mixture of hydrogen peroxide, solvent and propene is led over a succession of fixed bed reaction zones connected in series in down-flow operation. No temperature control means are present within the reactor to remove the generated heat from the single reaction zones. Thus, each reaction zone can be considered as an independent adiabatic reactor. In each reaction zone the reaction is performed to a partial conversion, the liquid reaction mixture is removed from each reaction zone, is led over an external heat exchanger to extract the heat of reaction, and the major portion of this liquid phase is then recycled to this reaction zone and a minor portion of the liquid phase is passed to the next zone. At the same time, gaseous propene is fed in together with the liquid feed stock mixture, is guided in a parallel stream to the liquid phase over the fixed bed reaction zones, and is extracted at the end of the reaction system in addition to the liquid reaction mixture as an oxygen-containing waste gas stream. Although this reaction procedure enables the propene oxide yield to be raised compared to conventional tubular reactors without the temperature control described in EP-A 659 473, it nevertheless involves considerable additional costs on account of the complexity of the reaction system required to carry out the process.

From U.S. Pat. No. 5,849,937 a process for epoxidation of propene using hydroperoxides especially organic hydroperoxides is known. The reaction mixture is fed to a cascade of serially connected fixed bed reactors in down-flow regime with respect to each single reactor. Similarly to the teaching of EP-A 659 473 in each reactor only partial conversion is accomplished and the reactors are not equipped with heat exchange means. As in EP-A 659 473, the reaction heat is removed by passing the effluent from each reactor through heat exchangers prior to introducing the reaction mixture to the next fixed bed reactor in series thereby adding to the complexity of the reaction system.

The disadvantages of the reaction systems as discussed in EP-A 659 473 and U.S. Pat. No. 5,849,937 are the complexity and thus the increased costs for investment and the high susceptibility to changes of process parameters like flow velocity due to the adiabaticly operated independent reaction zones and reactors, respectively.

WO 99/29416 discloses a reactor for the catalytic reaction of gaseous reaction media having a plate heat exchanger whereby the catalyst bed is located between the heat exchange plates and the cooling medium or heating medium is passed counter currently to the gaseous reaction phase through the heat exchange plates. There is neither reference to liquid phase or multiphase reaction media in general nor to oxidation or epoxidation reactions.

In view of the cited prior art, an object of the present invention is to provide a process for the epoxidation of olefins that results in improved conversion and product selectivity compared to WO 97/47614 while avoiding the disadvantages of the teachings of EP-A 659 473 and U.S. Pat. No. 5,849,937 which can be candied out using conventional reaction systems.

SUMMARY OF THE INVENTION

The above and other objects of the invention can be achieved by a process for the catalytic epoxidation of olefins with hydrogen peroxide in a continuous flow reaction system, wherein the reaction mixture comprising at least one liquid phase is passed through a fixed catalyst bed positioned between parallel heat exchange plates and the reaction heat is at least partially removed during the course of the reaction by passing a cooling medium through the heat exchange plates.

A particularly preferred embodiment of the present invention refers to a process for the catalytic epoxidation of propene with hydrogen peroxide in a continuous flow reaction system conducted in a multiphase reaction mixture comprising a liquid aqueous hydrogen peroxide rich phase containing methanol and a liquid organic propene rich phase, wherein the reaction mixture is passed through a fixed catalyst bed positioned between parallel heat exchange plates in down-flow operation mode and the reaction heat is at least partially removed during the course of the reaction by passing a cooling medium through the heat exchange plates.

The present inventors have surprisingly discovered, that by using a reactor with a bundle of parallel heat exchange plates wherein a fixed bed of catalyst is positioned between the heat exchange plates, the epoxidation of olefins with hydrogen peroxide can be conducted with high olefin oxide selectivity at high hydrogen peroxide conversion compared to tubular reactors with a cooling jacket. Without wishing to be bound by theory it is believed that this surprising effect is attributed to a more uniform heat dissipation when using the reactor type of the present invention.

Compared to tube bundle reactors the dimensions of the plate bundle reactor to be used in the process of the present invention are considerably reduced at the same space-time yield. Thus investment costs are considerably lower. Furthermore the reactor to be used according to the present invention is less susceptible to blocking and fouling compared to tube bundle reactors.

Although WO 99/29416 describes some advantages of a reactor having parallel heat exchange plates it is not derivable from that prior art that especially in liquid phase or multiple phase exothermic reaction systems the selectivity at high conversion can be increased compared to reactor types that are commonly used for example in epoxidation reactions.

DETAILED DESCRIPTION OF THE INVENTION

In the practice of the present invention any reactor having a fixed catalyst bed positioned between parallel heat exchange plates can be used. Tubular reactors with parallel heat exchange means, whereby the distance between heat exchange plates is in the range of 0.5 to 50 mm, preferably 10 to 30 mm, are particularly preferred. Adiabatic reaction conditions as taught in EP-A 659 473 and U.S. Pat. No. 5,849,937 should be avoided. As cooling medium that is pumped through the flow channels within the heat exchange plates all standard cooling media like oils, alcohols, liquid salts or water can be used. Water is most preferred. The cooling medium can be passed through the heat exchange plates counter-currently, co-currently or in cross-flow mode. A co-current flow is most preferred.

In one preferred embodiment of the present invention, the catalyst is packed between the heat exchange plates. Alternatively, the catalyst is coated on the outside surface of the heat exchange plates. When using the alternative embodiment particularly small distances between heat exchange plates can be adjusted, thereby increasing the total heat exchange surface area at constant reactor dimensions.

The process according to the invention for the epoxidation of olefins, preferably propene, is typically carried out at a temperature of 30° to 80° C., preferably at 40° to 60° C. According to a preferred embodiment of the present invention, the temperature profile within the reactor is maintained such that the cooling medium temperature of the cooling means is at least 40° C. and the maximum temperature within the catalyst bed is 60° C. at most, preferably 55° C. Preferably the temperature of the cooling medium is controlled by a thermostat.

The maximum temperature within the catalyst bed is measured with a plurality of suitable temperature measurement means like thermocouples or a Pt-100 arranged along the length of the reactor in suitable distances with respect to each other. By adjusting the number, position within the reactor and distances there-between, the temperature measurement means are controlled to measure the temperature of the catalyst bed within the entire reactor as exact as necessary.

The maximum temperature of the catalyst bed can be adjusted by different means. Depending on the selected reactor type, the maximum temperature of the catalyst bed can be adjusted by controlling the flow rate of the reaction mixture passing through the reactor, by controlling the flow rate of the cooling medium passing through the cooling means or by lowering the catalyst activity, for instance by diluting the catalyst with inert material.

The flow rate of the cooling medium is preferably adjusted to keep the temperature difference between entry of the cooling medium into the cooling means and exit below 5° C., preferably below 3° C., most preferably 2° C.

By selecting such a narrowly defined temperature profile within the reactor, an optimized balance between hydrogen peroxide conversion and olefin oxide selectivity can be achieved.

The pressure within the reactor is usually maintained at 5 to 50 bar preferably 15 to 30 bar.

Furthermore the present inventors realized that the combination of the reactor type used according to the present process and down-flow operation mode for the liquid reaction mixture results in surprisingly improved olefin selectivity at high hydrogen peroxide conversion.

In A. Gianetto, *"Multiphase Reactors: Types, Characteristics and Uses"*, in *Multiphase Chemical Reactors: Theory, Design, Scale-up,* Hemisphere Publishing Corporation, 1986 criteria governing the choice between up-flow and down-flow fixed bed multiphase reactors are given. Advantages of up-flow regime compared to down-flow regime are:

- better mixing resulting in improved heat and mass transfer;
- at the same fluid flow rates the up-flow operation provides higher volumetric gas/liquid mass transfer coefficients;
- better liquid distribution in the cross section;
- better heat dissipation and more uniform temperature;
- better wetting of the catalyst and therefore increased catalyst effectiveness;
- slower aging of the catalyst
- avoiding compacting of the catalyst bed.

Disadvantages are:

- larger pressure drops and higher energy expenditure for pumping;
- reactor has to include means to hold the catalyst in place in case of high velocities;
- higher mass transfer resistance inside the liquid and an increase in possible homogeneous side reactions can occur.

In view of the advantages with respect to heat transfer and dissipation up-flow operation of a fixed bed reactor for multiphase reaction systems is the natural choice for highly exothermic reactions where temperature control is important.

Contrary to the general textbook knowledge as exemplified by A. Gianetto supra, the present inventors discovered that a cooled fixed bed reactor can be successfully operated in a down-flow operation to increase product selectivity. As a result, overall product yield compared to an up-flow operation as previously used in the prior art. This effect is even more surprising since it is known that the epoxidation of olefin is a highly exothermic reaction that is difficult to control since this reaction has a considerably high activation temperature and therefore has to be conducted at a certain minimum temperature to achieve economically reasonable conversion. But on the other hand, the heat generated by the exothermic reaction has to be effectively removed from the reactor since at increased temperatures unwanted side reactions take place with the result that product selectivity is decreased. The effect of limited temperature increase within the catalyst bed is discussed to some extent in EP-A-659 473. With respect to the examples it is disclosed that in conventional tubular reactors temperature rise in the catalyst bed exceeds 15° C. whereas according to the examples in EP-A-659 473 the temperature rise is 8° C. at most and in the preferred embodiment 5½° C. Thus according to the teaching of EP-A-659 473, temperature rise within the catalyst bed has to be kept as low as possible in order to achieve high yields of propylene oxide. This reduced temperature rise could only be achieved according to EP-A-659 473 by conducting the reaction in a single reaction zone to only a partial conversion with the result that the majority of the reaction mixture has to be recycled, and by intermediately cooling the reaction mixture.

According to the teaching of A. Gianetto et al. when operating a conventional tubular fixed bed reactor poor heat dissipation and nonuniform temperature within the catalyst bed has to be expected in case of downflow operation mode. Thus it has to be expected that by using a downflow operation mode in a conventional cooled fixed bed reactor without intermediate external cooling of the reaction mixture, a high temperature rise within the catalyst bed due to poor heat dissipation would occur that should dramatically decrease product selectivity and thus the yield. But contrary to this expectation, using the process according to the present invention in down-flow operation mode leads to high olefin selectivity at high hydrogen peroxide conversion.

Another advantage of the reactor type to be used according to the present invention in down-flow operation mode of the reaction mixture compared to tube bundle reactors is that uniform feed of the liquid reaction mixture to the catalyst bed is much more easily to be accomplished. In tube bundle reactors, especially those that contain the catalyst bed within the tubes, means to supply the reaction mixture to each single tube have to be provided in down-flow operation to ensure uniform flow within the reactor resulting in very complicated and expensive equipment. In contrast thereto when using the plate bundle reactor according to the present invention, the flow channels for the reaction mixture between the heat exchange plates are much larger in the traverse direction so that the reaction mixture has to be supplied only to few locations along the width of one single flow channel to ensure uniform flow within the reactor. Furthermore, standard equipment used for liquid distribution in distillation columns can be used to feed the reaction mixture to the individual catalyst layers between the heat exchange plates. Preferably liquid distributors with tubes or channels parallel to the heat exchange plates and holes, slots or nozzles at regular intervals are used to supply the feed mixture. Such liquid distributors are known from K. Sattler, Thermische Treninverfahren, VCH Verlagsgesellschaft, 1995, table 2–35.

According to a preferred embodiment the reaction mixture is passed through the catalyst bed with a superficial velocity from 1 to 100 m/h, preferably 5 to 50 m/h, most preferred 5 to 30 m/h. The superficial velocity is defined as the ratio of volume flow rate/cross section of the catalyst bed. Consequently the superficial velocity can be varied in a given reactor by adjusting the flow rate of the reaction mixture.

Additionally it is preferred to pass the reaction mixture through the catalyst bed with a liquid hourly space velocity (LHSV) from 1 to 20 h$^{-1}$, preferably 1.3 to 15 h$^{-1}$.

Whenever the flow rate of the reaction mixture is adjusted to fulfill the above defined requirements for superficial velocity and liquid hourly space velocity particularly high selectivities can be achieved.

According to particularly preferred embodiment of the present invention, the process is conducted to maintain the catalyst bed in a trickle bed state. It has been surprisingly discovered that if the trickle bed state is maintained under certain flow conditions the effect of the present invention, i.e. the increased propene oxide selectivity will be particularly pronounced.

These conditions are as follows:

$G/\lambda < 2000$ m/h and $L\psi < 50$ m/h, wherein

G is the gaseous superficial velocity defined as the gaseous flow rate in m$^3$/h in the continuous flow reactor divided by the cross-section of the catalyst bed in m$^2$, L is the liquid superficial velocity defined as the liquid flow rate in m$^3$/h in the continuous flow reactor divided by the cross-section of the catalyst bed in m$^2$, $$\lambda = \left[\left(\frac{\rho_G}{\rho_W}\right)\left(\frac{\rho_L}{\rho_{Air}}\right)\right]^{1/2}, \text{ and } \psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in g/cm$^3$, $\rho_L$ is the density of the liquid phase in g/cm$^3$, $\rho_W$ is the density of water in g/cm$^3$, $\rho_{Air}$ is the density of air in g/cm$^3$, $\sigma_W$ is the surface tension of water in dyn/cm, $\sigma_L$ is the surface tension of the liquid phase in dyn/cm, $\mu_L$ is the viscosity of the liquid phase in centipoise, $\mu_W$ is the viscosity of water in centipoise.

In order to be able to operate the process continuously when changing and/or regenerating the epoxidation catalyst, two or more flow reactors may if desired also be operated in parallel or in series in the before-described manner.

Crystalline, titanium-containing zeolites especially those of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501. The titanium silicalite catalyst may be employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Extrudates with a diameter of 1 to 5 mm are preferably used as fixed bed catalysts.

When practicing the present invention it is preferred that the overall feed stream to the reactor comprises an aqueous hydrogen peroxide solution, an olefin and an organic solvent. Thereby these components may be introduced into the reactor as independent feeds or one or more of these feeds are mixed prior to introduction into the reactor.

Using the process according to the invention any olefins can be epoxidized, and in particular olefins, with 2 to 6 carbon atoms. The process according to the invention is most particularly suitable for the epoxidation of propene to propene oxide. For economic reasons it would be preferred for an industrial scale process to use propene not in a pure form but as a technical mixture with propane that as a rule contains 1 to 15 vol. % of propane. Propene may be fed as a liquid as well as in gaseous form into the reaction system.

The hydrogen peroxide is used in the process according to the invention in the form of an aqueous solution with a hydrogen peroxide content of 1 to 90 wt. %, preferably 10 to 70 wt. % and particularly preferably 30 to 50 wt. %. The hydrogen peroxide may be used in the form of the commercially available, stabilized solutions. Also suitable are unstabilized, aqueous hydrogen peroxide solutions such as are obtained in the anthraquinone process for producing hydrogen peroxide.

The reaction is preferably carried out in the presence of a solvent in order to increase the solubility of the olefin, preferably propene, in the liquid phase. Suitable as solvent are all solvents that are not oxidized or are oxidized only to a slight extent by hydrogen peroxide under the chosen reaction conditions, and that dissolve in an amount of more than 10 wt. % in water. Preferred are solvents that are completely miscible with water. Suitable solvents include alcohols such as methanol, ethanol or tert.-butanol; glycols such as for example ethylene glycol, 1,2-propanediol or 1,3-propanediol; cyclic ethers such as for example tetrahydrofuran, dioxane or propylene oxide; glycol ethers such as for example ethylene glycol monomethyl ether, ethylene glycol monoethyl ether, ethylene glycol monobutyl ether or propylene glycol monomethyl ether, and ketones such as for example acetone or 2-butanone. Methanol is particularly preferably used as solvent.

The olefin is preferably employed in excess relative to the hydrogen peroxide in order to achieve a significant consumption of hydrogen peroxide, the molar ratio of olefin, preferably propene, to hydrogen peroxide preferably being chosen in the range from 1.1 to 30. The solvent is preferably added in a weight ratio of 0.5 to 20 relative to the amount of hydrogen peroxide solution used. The amount of catalyst employed may be varied within wide limits and is preferably chosen so that a hydrogen peroxide consumption of more than 90%, preferably more than 95%, is achieved within 1 minute to 5 hours under the employed reaction conditions.

According to one embodiment of the present invention reaction conditions like temperature, pressure, selection of olefin and selection of solvent and relative amounts of the components of the reaction mixture are chosen to ensure the presence of only one liquid phase wherein both the olefin and the hydrogen peroxide are dissolved. An additional gaseous olefin containing phase may also be present.

In another embodiment of the invention, the epoxidation of olefins with hydrogen peroxide is conducted in a multiphase reaction mixture comprising a liquid aqueous hydrogen peroxide rich phase containing an organic solvent having a solubility in water of at least 10% by weight at 25° C. and a liquid organic olefin rich phase. Thereby an even better product selectivity can be achieved.

As will be appreciated by any person skilled in the art, the presence of two immiscible liquid phases in a reaction system comprising an olefin, an water miscible organic solvent and an aqueous hydrogen peroxide solution will depend on many different factors. First of all, the presence of an additional olefin rich liquid organic phase will depend on the temperature and pressure applied in the reactor and the selected olefin. Preferably, the applied pressure is at or above the vapor pressure of the olefin at the chosen temperature. Furthermore it will depend on the selection of the organic solvent. Suitable as organic solvent are all solvents that dissolve in an amount of more than 10 wt. % in water at 25° C. Preferred are solvents that dissolve in an amount of more than 30 wt. % in water at 25° C. preferably more than 50 wt. % in water at 25° C. The most preferred solvents are completely miscible with water. In principle all solvents as exemplified above can also be used in this preferred embodiment as long as the conditions are met to ensure the presence of two liquid phases.

Additionally the presence of a second organic olefin rich phase will depend on the relative amounts of olefin, water and solvent. The amount of solvent is chosen to achieve sufficient solubility of the olefin in the hydrogen peroxide rich aqueous phase in order to get the desired rate of reaction. At a given temperature, pressure, olefin and solvent the relative amounts of ingredients can be adjusted to ensure formation of a second liquid organic phase. That is, to ensure the formation of a second liquid organic olefin rich phase, the amount of olefin has to be selected in excess of the amount soluble in the aqueous phase at the chosen temperature and pressure.

A simple means of experimentally confirming the presence of a second liquid organic phase at the reaction conditions is by collecting a sample of the reaction mixture in a container equipped with a sight glass at the temperature and pressure used in the process. Alternatively, the reactor may be equipped with a sight glass at a suitable position to observe the phase boundary directly during the reaction. In case of a continuous flow reactor the sight glass is preferably positioned near the outlet of the reactor effluent to have an optimal control that two liquid phases are present through out the entire residence time within the reactor.

Thus, a person skilled in the art can without any effort verify whether when applying certain selections for olefins, solvents and reaction parameters a two-liquid phase system as required by the present invention is present and can adjust by variation of the parameters as discussed above in detail the reaction system in order to establish a second liquid organic phase.

According to a most preferred embodiment of the present invention the olefin is selected to be propene, and methanol is used as a solvent. For example, for a reaction mixture comprising propene, methanol, and aqueous hydrogen peroxide at a reaction temperature between 30° C. and 80° C., a pressure from 5 to 50 bar the ratio of propene flow to total flow in case of a continuous flow system can be adjusted to be in the range of 0.1 to 1, preferably 0.2 to 1 in order to obtain a second liquid organic phase.

An additional gas phase comprising olefin vapor and optionally an inert gas, i.e. a gas that does not interfere with the epoxidation can be additionally present according to the present invention. Adding an inert gas is useful to maintain a constant pressure inside the reactor and to remove oxygen gas formed by the decomposition of a small part of the hydrogen peroxide charged to the reactor.

The present invention refers to a process for the catalytic epoxidation of olefins with hydrogen peroxide in a continuous flow reaction system, wherein the reaction mixture comprising at least one liquid phase is passed through a fixed catalyst bed positioned between parallel heat exchange plates and the reaction heat is at least partially removed during the course of the reaction by passing a cooling medium through the heat exchange plates.

According to a preferred embodiment, the heat exchange plates are positioned within a tubular reactor and the distance between heat exchange plates is in the range of 0.5 to 50 mm, preferably 10 to 30 mm.

Preferably, the catalyst is packed between the heat exchange plates.

Alternatively, the catalyst is coated on the outside surface of the heat exchange plates.

According to a preferred embodiment of the present invention, the reaction mixture is passed through the catalyst bed with a superficial velocity from 1 to 100 m/h, preferably 5 to 50 m/h, most preferably 5 to 30 m/h.

Preferably, the reaction mixture is passed through the catalyst bed with a liquid hourly space velocity (LHSV) from 1 to 20 h$^{-1}$, preferably 1.3 to 15 h$^{-1}$.

According to a particularly preferred embodiment of the present invention, the reaction mixture is passed through the catalyst bed in down-flow operation mode.

Preferably, the fixed catalyst bed is maintained in a trickle bed state.

More preferred, the trickle bed state is maintained tinder following flow conditions:

G/λ<2000 m/h and

Lψ<50 m/h, wherein

G is the gaseous superficial velocity defined as the gaseous flow rate in m$^3$/h in the continuous flow reaction system divided by the cross-section of the catalyst bed in m$^2$, L is the liquid superficial velocity defined as the liquid flow rate in m$^3$/h in the continuous flow reaction system divided by the cross-section of the catalyst bed in m$^2$, $$\lambda = \left[\left(\frac{\rho_G}{\rho_W}\right)\left(\frac{\rho_L}{\rho_{Air}}\right)\right]^{1/2}, \text{ and } \psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in g/cm$^3$, $\rho_L$ is the density of the liquid phase in g/cm$^3$, $\rho_W$ is the density of water in g/cm$^3$, $\rho_{Air}$ is the density of air in g/cm$^3$, $\sigma_W$ is the surface tension of water in dyn/cm, $\sigma_L$ is the surface tension of the liquid phase in dyn/cm, $\mu_L$ is the viscosity of the liquid phase in centipoise, $\mu_W$ is the viscosity of water in centipoise.

According to a preferred embodiment, distribution means selected from tubes or channels parallel to the heat exchange plates and holes, slots or nozzles at regular intervals are used to feed the reaction mixture to the individual catalyst layers between the heat exchange plates.

Preferably, the reaction temperature is from 30 to 80° C., more preferred from 40 to 60° C., whereby preferably a temperature profile within the reactor in maintained such that the cooling medium temperature of the cooling means is at least 40° C. and the maximum temperature within the catalyst bed is 60° C. at the most.

The pressure within the reactor is preferably maintained at 5 to 50 bar, more preferred at 15 to 30 bar.

According to a preferred embodiment, the overall feed stream to the reactor comprises an aqueous hydrogen peroxide solution, an olefin and an organic solvent.

Thereby the reaction is preferably conducted in a multiphase reaction mixture comprising an liquid aqueous hydrogen peroxide rich phase containing an organic solvent having a solubility in water of at least 10% by weight at 25° C. and an liquid organic olefin rich phase.

Preferably, the organic solvent is methanol, the catalyst is titanium-containing zeolite and the olefin is propene.

According to a particularly preferred embodiment, the present invention relates to a process for the catalytic epoxidation of propene with hydrogen peroxide in a continuous flow reaction system wherein a reaction mixture comprising hydrogen peroxide, methanol and propene is passed through a fixed catalyst bed positioned between parallel heat exchange plates in down-flow operation mode and the reaction heat is at least partially removed during the course of the reaction by passing a cooling medium through the heat exchange plates.

In carrying out the preferred embodiment of the invention, a reactor such as shown in WO 99/29416 can be used, which is relied on and incorporated herein by reference.

Preferably, the reaction mixture in that embodiment is a multiphase reaction mixture comprising an liquid aqueous hydrogen peroxide rich phase containing methanol and a liquid organic propene rich phase.

Further variations and modifications of the foregoing will be apparent to those skilled in the art and are intended to be encompassed by the claims appended hereto.

What is claimed is:

1. A process for the catalytic epoxidation of olefins with hydrogen peroxide in a continuous flow reaction system, comprising passing a reaction mixture comprising at least one liquid phase through a fixed catalyst bed positioned between parallel heat exchange plates and heat of reaction is at least partially removed during the course of reaction by passing a cooling medium through the heat exchange plates.

2. The process of claim 1, wherein the heat exchange plates are positioned within a tubular reactor and the distance between heat exchange plates is in the range of 0.5 to 50 mm.

3. The process of claim 1, wherein the heat exchange plates are positioned within a tubular reactor and the distance between heat exchange plates is in the range of 10 to 30 mm.

4. The process of claim 1, wherein the catalyst is packed between the heat exchange plates.

5. The process of claim 2, wherein the catalyst is packed between the heat exchange plates.

6. The process of claim 3, wherein the catalyst is packed between the heat exchange plates.

7. The process of claim 1, wherein the catalyst is coated on the outside surface of the heat exchange plates.

8. The process of claim 2, wherein the catalyst is coated on the outside surface of the heat exchange plates.

9. The process of claim 3, wherein the catalyst is coated on the outside surface of the heat exchange plates.

10. The process of claim 1, further comprising passing the reaction mixture through the catalyst bed with a superficial velocity from 1 to 100 m/h.

11. The process of claim 1, further comprising passing the reaction mixture through the catalyst bed with a superficial velocity from 5 to 50 m/h.

12. The process of claim 1, further comprising passing the reaction mixture through the catalyst bed with a superficial velocity from 5 to 30 m/h.

13. The process of claim 1, further comprising passing the reaction mixture through the catalyst bed with a liquid hourly space velocity (LHSV) from 1 to 20 h$^{-1}$.

14. The process of claim 1, further comprising passing the reaction mixture through the catalyst bed with a liquid hourly space velocity (LHSV) from 1.3 to 15 h$^{-1}$.

15. The process of claim 1, wherein the reaction mixture is passed through the catalyst bed in down-flow operation mode.

16. The process of claim 15, wherein the fixed catalyst bed is maintained in a trickle bed state.

17. The process of claim 16, further comprising maintaining the trickle bed state under the following conditions:

G/λ<2000 m/h and

Lψ<50 m/h.

wherein,

G is the gaseous superficial velocity defined as the gaseous flow rate in m$^3$/h in the continuous flow reaction system divided by the cross-section of the catalyst bed in m$^2$.

L is the liquid superficial velocity defined as the liquid flow rate in m$^3$/h in the continuous flow reaction system divided by the cross-section of the catalyst bed in m$^2$, $$\lambda = \left[\left(\frac{\rho_G}{\rho_W}\right)\left(\frac{\rho_L}{\rho_{Air}}\right)\right]^{1/2}, \text{ and } \psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in g/cm$^3$, $\rho_L$ is the density of the liquid phase in g/cm$^3$, $\rho_W$ is the density of water in g/cm$^3$, $\rho_{Air}$ is the density of air in g/cm$^3$, $\sigma_W$ is the surface tension of water in dyn/cm, $\sigma_L$ is the surface tension of the liquid phase in dyn/cm, $\mu_L$ is the viscosity of the liquid phase in centipoise, $\mu_W$ is the viscosity of water in centipoise.

18. The process of claim 1, further comprising feeding the reaction mixture to individual catalyst layers between the heat exchange plates through distribution means selected from tubes or channels parallel to the heat exchange plates and holes, slots or nozzles at regular intervals.

19. The process of claim 1, wherein reaction temperatures range from 30 to 80° C.

20. The process of claim 1, wherein reaction temperatures range from 40 to 60° C.

21. The process of claim 20, wherein a temperature profile within the reactor is maintained such that the cooling medium temperature of the cooling means is at least 40° C. and the maximum temperature within the catalyst bed is 60° C. at the most.

22. The process of claim 1, wherein the pressure within the reactor is maintained at 5 to 50 bar.

23. The process of claim 1, wherein the pressure within the reactor is maintained at 15 to 30 bar.

24. The process of claim 1, wherein the overall feed stream to the reactor comprises an aqueous hydrogen peroxide solution, an olefin and an organic solvent.

25. The process of claim 24, further comprising carrying out a reaction with a multiphase reaction mixture comprising a liquid aqueous hydrogen peroxide rich phase containing an organic solvent having a solubility in water of at least 10% by weight at 25° C. and a liquid organic olefin rich phase.

26. The process of claim 24, wherein the organic solvent is methanol.

27. The process of claim 1, wherein a titanium-containing zeolite is the catalyst.

28. The process of claim 1, wherein the olefin is propene.

29. A process for the catalytic epoxidation reaction of propene with hydrogen peroxide in a continuous flow reaction system comprising passing a reaction mixture comprising hydrogen peroxide, methanol and propene through a fixed catalyst bed positioned between parallel heat exchange plates in down-flow operation mode and at least partially removing heat of said reaction during the course of said reaction by passing a cooling medium through the heat exchange plates.

30. The process of claim 29, wherein the reaction mixture is a multiphase reaction mixture comprising a liquid aqueous hydrogen peroxide rich phase containing methanol and a liquid organic propene rich phase.

* * * * *

UNITED STATES PATENT AND TRADEMARK OFFICE
CERTIFICATE OF CORRECTION

PATENT NO.    : 6,610,865 B2                                        Page 1 of 1
DATED         : August 26, 2003
INVENTOR(S)   : Hofen Willi et al.

It is certified that error appears in the above-identified patent and that said Letters Patent is hereby corrected as shown below:

<u>Title page,</u>
Item [22], Filed:, should read as follows:
-- Aug. 15, 2002 --
Item [56], References Cited, FOREIGN PATENT DOCUMENTS, should read as follows:

| | | | |
|---|---|---|---|
| -- | DE | 198 35 907 | 2/2000 |
| | DE | 19723950 | 12/1998 |
| | EP | 0 100 118 | 2/1984 |
| | EP | 0 100 119 | 2/1984 |
| | EP | 0 230 349 | 7/1987 |
| | EP | 0 230 949 | 8/1987 |
| | EP | 0 568 336 | 11/1993 |
| | EP | 0 568 337 A2 | 11/1993 |
| | EP | 0 583 828 | 2/1994 |
| | EP | 0 645 473 | 3/1995 |
| | EP | 0 659 473 A1 | 6/1995 |
| | EP | 0 712 852 | 5/1996 |
| | EP | 0 719 768 | 7/1996 |
| | EP | 0 757 045 | 2/1997 |
| | EP | 0 795 537 | 9/1997 |
| | EP | 0 827 765 | 3/1998 |
| | EP | 0 930 308 | 7/1999 |
| | EP | 0 936 219 | 8/1999 |
| | EP | 1 122 248 | 8/2001 |
| | EP | 1 221 442 | 7/2002 |
| | EP | 1 138 387 | 10/2001 |
| | JP | 2166636 | 6/1990 |
| | WO | WO 97/47613 | 12/1997 |
| | WO | WO 97/47614 | 12/1997 |
| | WO | WO 99/01445 | 1/1999 |
| | WO | WO 99/07690 | 2/1999 |
| | WO | WO 99/11639 | 3/1999 |
| | WO | WO 00/07695 | 2/2000 |
| | WO | WO 00/17178 | 3/2000 -- |

Item [74], *Attorney, Agent or Firm*, should read as follows:
-- Smith, Gambrell & Russell. LLP --

Signed and Sealed this

Sixth Day of April, 2004

JON W. DUDAS
*Acting Director of the United States Patent and Trademark Office*